(12) United States Patent
Cummins

(10) Patent No.: US 7,554,134 B2
(45) Date of Patent: Jun. 30, 2009

(54) INTEGRATED CMOS POROUS SENSOR

(75) Inventor: Timothy Cummins, Clare County (IE)

(73) Assignee: ChipSensors Limited, Limerick (IE)

( * ) Notice: Subject to any disclaimer, the term of this patent is extended or adjusted under 35 U.S.C. 154(b) by 456 days.

(21) Appl. No.: 11/092,725

(22) Filed: Mar. 30, 2005

(65) Prior Publication Data

US 2005/0218465 A1  Oct. 6, 2005

Related U.S. Application Data

(60) Provisional application No. 60/558,565, filed on Apr. 2, 2004.

(51) Int. Cl.
H01L 29/80  (2006.01)

(52) U.S. Cl. .......................... 257/252; 257/368; 257/758

(58) Field of Classification Search ................. 257/253, 257/368, 369, 414, 773, 252, 758
See application file for complete search history.

(56) References Cited

U.S. PATENT DOCUMENTS

| | | | |
|---|---|---|---|
| 4,057,823 A * | 11/1977 | Burkhardt et al. ............ | 257/414 |
| 5,801,428 A | 9/1998 | Felde et al. .................. | 257/414 |
| 6,017,775 A | 1/2000 | Igel et al. .................... | 438/48 |
| 6,111,280 A | 8/2000 | Gardener et al. ............. | 257/253 |
| 6,417,026 B2 * | 7/2002 | Gotoh et al. ................. | 438/108 |
| 6,690,569 B1 | 2/2004 | Mayer et al. ................. | 361/303 |
| 2004/0008471 A1 | 1/2004 | Davis et al. .................. | 361/306 |

OTHER PUBLICATIONS

Lemme, Elektronik vol. 43, No. 24, Nov. 29, 1994, pp. 57-66, CMOS-Sensoren gehort die Zukunft.
Bousse et al, IEEE Electron Device Ltrs, vol. 9, No. 1, Jan. 1988, pp. 44-46, A Process for the Combined Fabrication of Ion . . . .
Patent Abstracts of Japan, vol. 12, No. 350, Sep. 20, 1988 & JP 63103957A (Seiko Epson Corp), May 9, 1988.
Baltes et al, Proc of the IEEE, vol. 86, No. 8, Aug. 1998, pp. 1660-1678, Micromachined Thermally Based CMOS Microssensors.
Baltes et al, Proc of the IEEE, vol. 35, No. 9, Sep. 9, 1998, pp. 35-38, The electronic nose in Lilliput.

* cited by examiner

Primary Examiner—Matthew Smith
Assistant Examiner—Candice Y Chan
(74) Attorney, Agent, or Firm—Jacobson Holman PLLC

(57) ABSTRACT

A single chip wireless sensor (1) comprises a microcontroller (2) connected by a transmit/receive interface (3) to a wireless antenna (4). The microcontroller (2) is also connected to an 8 kB RAM (5), a USB interface (6), an RS232 interface (8), 64 kB flash memory (9), and a 32 kHz crystal (10). The device (1) senses humidity and temperature, and a humidity sensor (11) is connected by an 18 bit ΣΔ A-to-D converter (12) to the microcontroller (2) and a temperature sensor (13) is connected by a 12 bit SAR A-to-D converter (14) to the microcontroller (2). The device (1) is an integrated chip manufactured in a single process in which both the electronics and sensor components are manufactured using standard CMOS processing techniques, applied to achieve both electronic and sensing components in an integrated process.

16 Claims, 10 Drawing Sheets

$\Phi_{F1} = nXOR(Q1, \Phi_1)$
$\Phi_{F2} = nXOR(Q1, \Phi_2)$ $\Phi_{G1} = nXOR(Q2, \Phi_1)$
$\Phi_{G2} = nXOR(Q2, \Phi_2)$

INTEGRATED CMOS POROUS SENSOR

This is a complete application claiming benefit of U.S. Provisional 60/558,565 filed Apr. 2, 2004.

FIELD OF THE INVENTION

The invention relates to electronic sensors.

PRIOR ART DISCUSSION

One of the main driving forces in the electronics industry is the desire to achieve greater integration of functionality so that production is more automated and per-unit cost reduced. An added benefit is, of course, decreased size and thus higher circuit density. Most importantly, for battery applications, higher integration generally results in lower power, due to reduced parasitic capacitances.

However in the field of sensors, and in particular wireless sensors, greater integration has been slow because of the difficulties encountered in integration of microcontroller, A-to-D converter (ADC), memory, RF transceiver, and sensor elements in the one integrated sensor device. These difficulties have arisen because of incompatibilities of materials processing for the various elements. For example, sensor elements have conventionally been manufactured on ceramic or glass substrates and can not be easily integrated on silicon. RF transceivers have typically been made from bipolar transistors, which are difficult to integrate with other technologies such as CMOS. Also, many CMOS high-resolution ADCs are made using poly-poly capacitors, which suffer from substrate parasitics, strain, and mis-match effects. Also, the aluminium metallisation used in IC processing is prone to corrosion, thus limiting usefulness for some types of sensor applications.

U.S. Pat. Nos. 6,724,612 and 6,690,569 describe sensor devices having both electronic and sensing components, the latter being capacitive electrodes. However, the electrodes require platinum or gold coating, and deposition of a polymer as a moisture-sensing dielectric. This processing is not amenable to high-volume semiconductor processing.

The invention addresses these issues.

SUMMARY OF THE INVENTION

According to the invention, there is provided an integrated sensor device comprising:
  MOS circuits in a semiconductor substrate,
  interconnect levels with interconnect conductors and insulating dielectric, said levels being over the substrate and interconnecting the MOS circuits,
  the interconnect levels incorporating a sensor having electrodes embedded in the interconnect dielectric, and
  the MOS circuits including a processor for processing signals from the sensor electrodes.

In one embodiment, the sensor comprises a porous oxide for ingress of a gas or humidity being sensed.

In another embodiment, the porous oxide is carbon-doped $SiO_2$.

In a further embodiment, the sensor is a capactive sensor.

In one embodiment, the sensor comprises a passivation layer over the sensor electrodes.

In another embodiment, the porous oxide is deposited on the passivation layer, and the MOS circuits detect changes in a fringe field between the electrodes.

In a further embodiment, comprises etch stop layers between the interconnect levels, and the passivation layer is of the same composition as the etch stop material.

In one embodiment, the passivation layer is of $Si_3N_4$ composition.

In another embodiment, the passivation layer is recessed over the sensing electrodes.

In a further embodiment, there is a porous oxide film in the recess.

In one embodiment, the porous oxide is between the electrodes and is exposed.

In another embodiment, the MOS circuits are directly beneath the sensor in a vertical dimension.

In a further embodiment, the MOS circuits include a temperature sensor.

In one embodiment, the temperature sensor comprises a PNP transistor.

In another embodiment, the MOS circuits include a microcontroller for processing both gas or humidity signals from the gas or humidity sensor and temperature signals from the temperature sensor to provide an enhanced output.

In a further embodiment, the enhanced output is temperature-corrected gas or humidity readings.

In one embodiment, the sensor comprises polyimide deposited over the sensor electrodes.

In another embodiment, the MOS circuits include an A-to-D converter connected between the sensor electrodes and the processor.

In a further embodiment, the A-to-D converter comprises an array of dummy capacitors with a constant topography surrounding active A-to-D converter capacitors.

In one embodiment, further comprises a light emitting diode.

In another embodiment, said diode is formed in a deep trench to a lower interconnect level laterally of the sensor electrodes.

In a further embodiment, the device comprises a photo-detector diode.

In one embodiment, said diode is in a deep trench in a lower interconnect level laterally of the sensor electrodes.

In another embodiment, the MOS circuits include a wireless transceiver.

In a further embodiment, the wireless transceiver is for communication with other nodes in a network, and it comprises a means for switching channel frequency according to a low frequency channel switching scheme upon detection of interference.

In one embodiment, an interconnect level includes a low noise amplifier.

In another embodiment, the low noise amplifier comprises a strained silicon region beneath a conductor.

In a further embodiment, the strained silicon is in a fifth or sixth interconnect level above the substrate.

In one embodiment, the sensor comprises a detecting element connected between pads on an upper surface of the device.

In another embodiment, the element is a gas-sensing thin film.

In a further embodiment, the element is of zinc oxide composition.

In one embodiment, said element detects sound and the MOS circuits comprise an audio processor for processing signals from the elements.

In another aspect of the invention, there is provided a method of producing a sensor device of any of the above embodiments, the method comprising the steps of:
  fabricating the MOS circuits in the substrate,
  fabricating the interconnect levels in successive fabrication cycles according to interconnect design to interconnect the MOS circuits, and fabricating the sensor electrodes and dielectric in a final interconnect level.

In one embodiment, the method comprises the further step of depositing a passivation layer over the top interconnect level.

In another embodiment, the method comprises the steps of depositing an etch stop layer over each layer of dielectric in the interconnect levels, and depositing etch stop material over the top interconnect level dielectric to provide a passivation layer.

In a further embodiment, porous oxide is provided as a dielectric in lower interconnect levels and regular oxide is used as a dielectric in upper interconnect levels.

In one embodiment, a strained low noise amplifier is deposited in an upper interconnect level, said amplifier comprising a strained silicon region.

DETAILED DESCRIPTION OF THE INVENTION

Brief Description of the Drawings

The invention will be more clearly understood from the following description of some embodiments thereof, given by way of example only with reference to the accompanying drawings in which.

DESCRIPTION OF THE EMBODIMENTS

Gas/Humidity Sensor Embodiment

Figure 1:
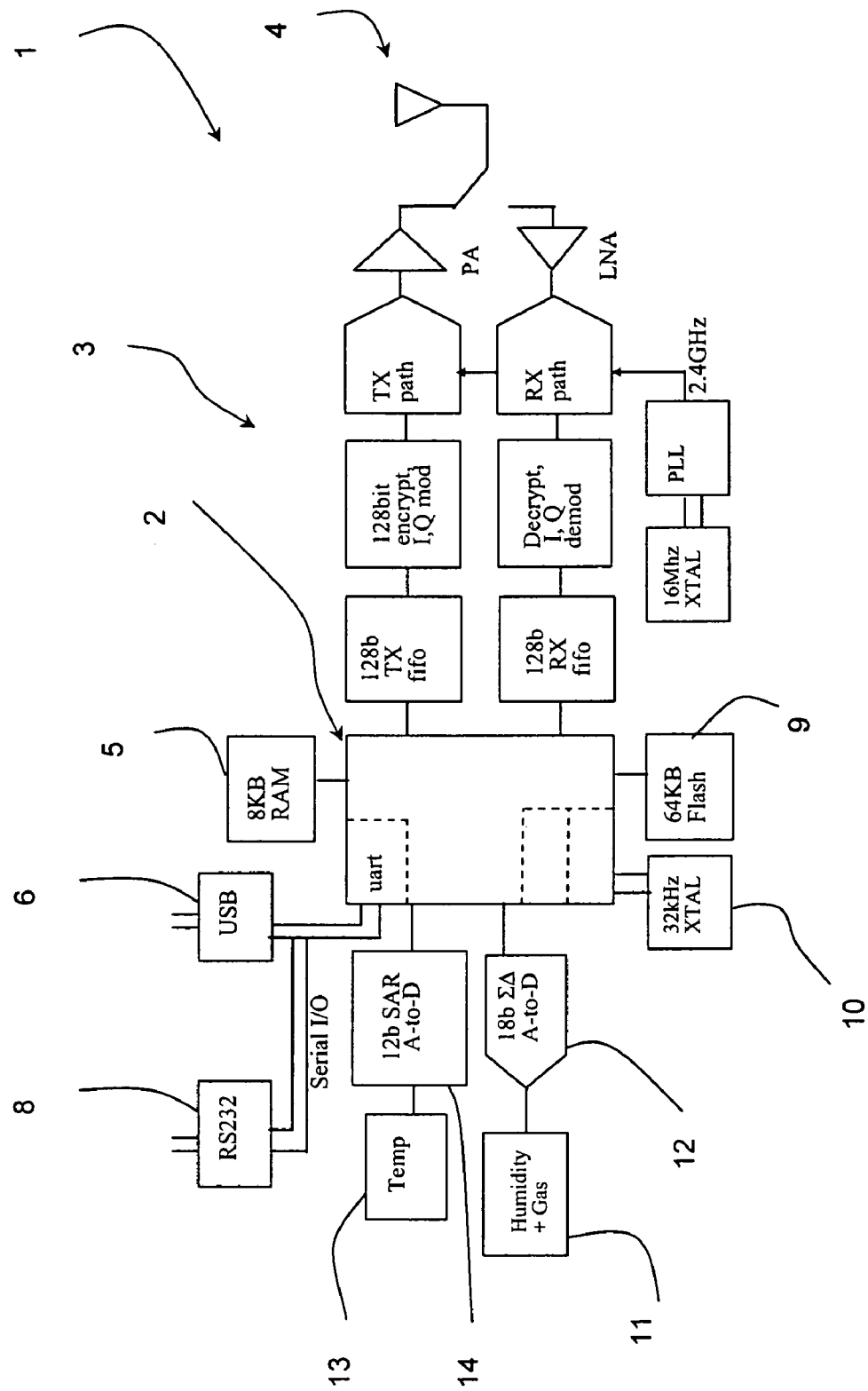
FIG. 1 is a block diagram of a single-chip wireless sensor device of the invention.
Figure 2:
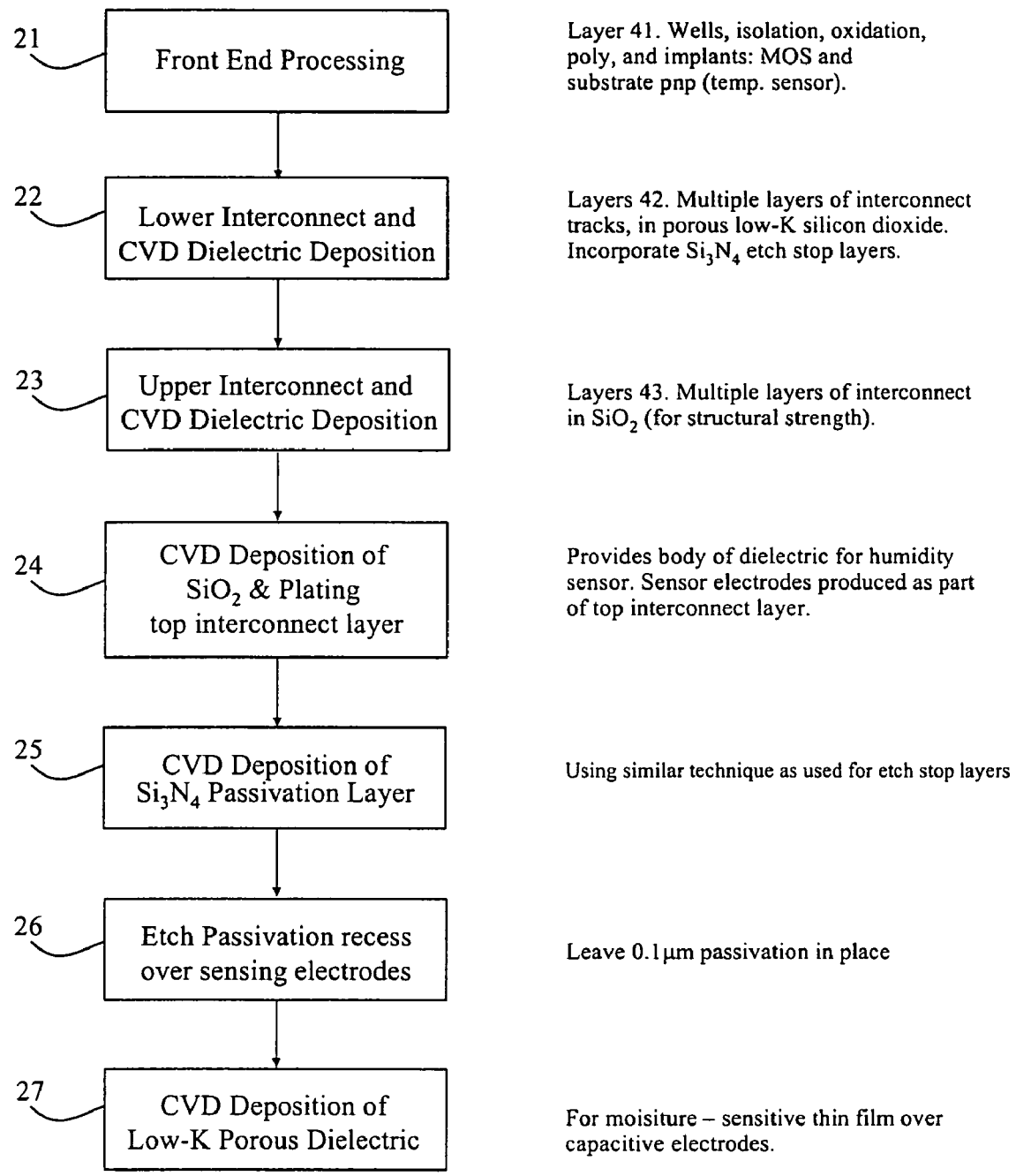
FIG. 2 is a flow diagram illustrating a process for producing the device.

Referring to FIG. 1 a single chip wireless sensor 1 comprises a microcontroller 2 connected by a transmit/receive interface 3 to a wireless antenna 4. The microcontroller 2 is also connected to an 8 kB RAM 5, a USB interface 6, an RS232 interface 8, 64 kB flash memory 9, and a 32 kHz crystal 10. In this embodiment, the device 1 senses humidity and temperature, and a humidity sensor 11 is connected by an 18 bit $\Sigma\Delta$ A-to-D converter 12 to the microcontroller 2 and a temperature sensor 13 is connected by a 12 bit SAR A-to-D converter 14 to the microcontroller 2.

The device 1 is a single integrated chip manufactured in a single process in which both the electronics and sensor components are manufactured using standard CMOS processing techniques, applied to achieve both electronic and sensing components in an integrated process.

The manufacturing process 20 is now described in more detail referring to FIGS. 2, 3(a), 3(b) and 3(c), and the steps are 21 to 27 inclusive.

21, Front End Processing

A substrate 41 of silicon is processed with CMOS wells, isolation oxidation, poly-silicon, and implants to form MOS components, as is well known in CMOS processing. Also, in the substrate a temperature-sensitive PNP transistor is formed to provide the sensor 13.

22, Lower Interconnect and Dielectric Deposition

First, second, and third interconnect levels 42 are formed. This involves three cycles of chemical vapour deposition (CVD) deposition of a porous low-K silicon dioxide dielectric 42(a), and etching and copper plating operations to provide interconnect tracks 42(b). Each cycle finishes in deposition of an etch stop layer 42(c) for limiting the extent of etching in the next cycle. The etch stop material is silicon nitride $Si_3N_4$. The silicon dioxide, the interconnect metal, and the etch stop of each cycle forms a first interconnect three-level stack 42. The use of a low-K dielectric allows low capacitance for faster signal transfer between components.

23, Upper Interconnect and CVD Dielectric Deposition

Fourth and fifth interconnect levels 43 are formed. There are a further two cycles of dielectric deposition and metal interconnect plating. However, in these two cycles the dielectric is "regular" $SiO_2$ (non-porous) 43(a) for better structural strength, to counteract the weaker mechanical strength of the porous dielectric in the lower levels 42. Again, these cycles involve standard CMOS techniques.

The fifth level includes a heating element 43(b) with an internal temperature monitor for instantaneous heating and purging of the humidity sensor 11 with immediate temperature monitoring. Also, as part of developing the fourth and fifth levels, the process adds a thin metal plate for a capacitor top metal (CTM) with a thin layer (0.04 μm) $SiO_2$ dielectric between them to form mixed signal metal-insulator-metal (MIM) capacitors for both of the A-to-D converters.

24, CVD Deposition of $SiO_2$, Sensing level

An interconnect/sensing layer 44 is formed. This is simply a next iteration or cycle following from the previous interconnect and plating cycles and indeed the dielectric is the same as for the immediately preceding cycles, "regular" $SiO_2$. However as an integral part of plating the top interconnect layer 44 humidity-sensing capacitive interdigitated fingers (electrodes) 45 and reference capactive interdigitated fingers (electrodes) 46 are formed. The size and spacing of the fingers is chosen to suit the application. In this embodiment the fingers 45 and 46 have a spacing of 0.5 μm. The arrangement is shown more clearly in FIG. 3(b). Using oxide permittivity Kox of 3.9, this results in capacitance of:

$$Cox = \frac{k_{ox}e_0}{Tox} = \frac{3.9 * 8.85 \times 10^{-12}}{0.5 \times 10^{-6}} = 0.000069 \; F/m^2 = 0.069 \; fF/\mu m^2$$

Each actual capacitive structure is about the size of a bond pad, allowing each finger to have a total length of 4000 μm. For a metal thickness of 1 μm this gives a sensor capacitance of 0.276 pF. However, the capacitance between two closely-spaced narrow conductors can be about 10% to 30% greater than the simple parallel plate calculated value, due to fringing components.

25, Deposition of $Si_3N_4$ Passivation Layer

A passivation layer 48 is deposited by CVD in a manner similar to that of the conventional etch stop layers as it is also of $Si_3N_4$. The passivation layer 48 is, however, approximately 3-5 μm thick to offer physical protection and a moisture barrier for the device 1.

26, Etch Passivation Over Sensing Electrodes

That part of the passivation layer 48 over the sensing electrodes 45 is etched to a depth of 90% to leave a thin $Si_3N_4$ layer 48(*a*) of approximately 0.1 μm depth over the sensing electrodes.

27, CVD Deposition of Porous Oxide

The same material as is used as a dielectric in the first three levels is now deposited by CVD in the recess formed in step 26. This is a moisture-sensing film 49 having a large specific area. Ingress of gas or moisture causes a change in permittivity of the porous dielectric. This causes a change in capacitance of the underlying sensing electrodes 45.

It will be appreciated from the above that standard Deep-Sub-Micron CMOS processing techniques are used, thus achieving fully integrated production. The sensor is made simultaneously with the rest of the chip, using the same dielectric and interconnect metal layers. This 'standard CMOS' method is very advantageous to the high-volume manufacturability of this sensor 1.

This approach has not apparently been attempted heretofore because of the perception that such a sensor would require polymers, and gold or platinum plating and/or other non-standard materials which would be regarded as contaminants in a modern CMOS wafer fabrication plant. Developments in $SiO_2$-based compositions to achieve reduced capacitance break up the internal lattice structure. This makes them porous and amenable to moisture or gas penetration. Also, the silicon nitride ($Si_3N_4$) of CMOS processing to achieve an etch stop layer is used in the sensor architecture to act as a barrier layer to protect the integrated device. In the above embodiment the $Si_3N_4$ layer is over the sensing component and it acts as a barrier to ingress of the moisture being sensed as such penetration may corrode the electrodes in high humidity environments. The sensing is therefore based on use of the spring effect, as set out below.

Use of Device 1

In use, moisture ingresses into the film 49 so that it affects its dielectric constant, and therefore the fringe field, between the sensing fingers 45. This is illustrated by the lines 55 in FIG. 3(*c*). This occurs even though the moisture is blocked by the thin part 48(*a*) of the layer 48 from accessing the spaces between the sensing fingers 45.

Figure 4:
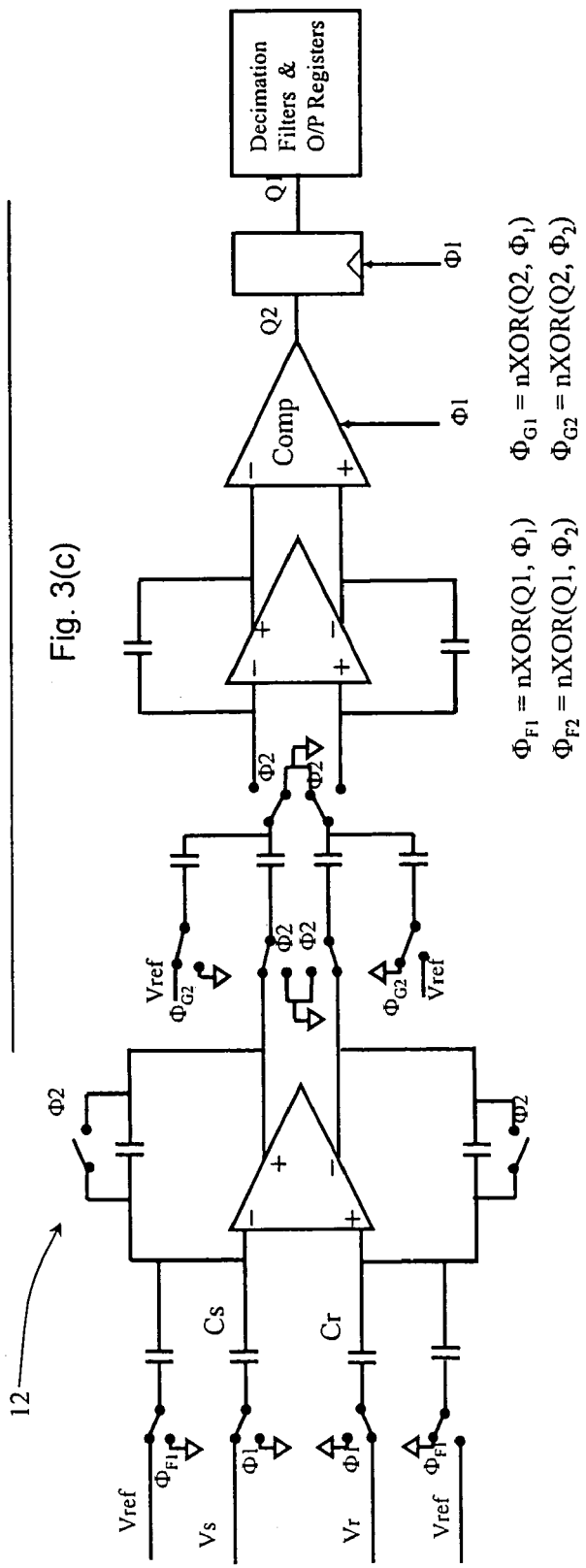
FIG. 4 is a schematic of an A-to-D converter of the device.

The sensor 1 relies on this fringe component 55 of the field between the electrodes. For the 4000 μm, 0.27 pF structure described, the fringe component is about 25 to 50 fF. Because of the close proximity of the 18-bit ΣΔ A-to-D converter (immediately beneath the sensor) very small capacitance changes are detectable, even in the fringe field. This converter is shown in FIG. 4 in which the sensing fingers 45 are Cs and the reference fingers 46 are Cr. These capacitances form the differential front-end of a second-order over-sampled sigma-delta modulator, illustrating the level of integration between the sensor and converter components. Vr and Vs provide scale and offset compensation. Very high resolution is achieved by trading off the number of samples per second and over-sampling ratio using the decimation filters.

Figure 5:
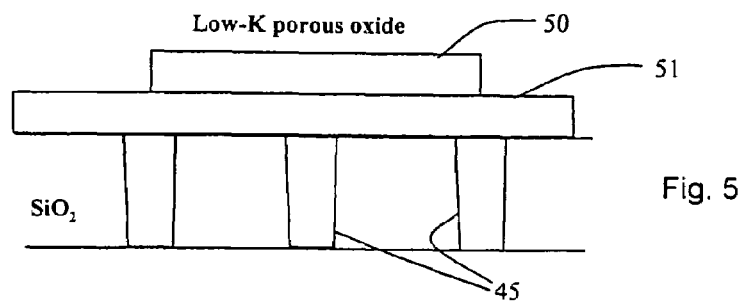
FIG. 5 is a diagram showing a sensor component of an alternative embodiment.

Referring to FIG. 5, in this embodiment, porous material 50 is deposited (or printed) on top of passivation 51, eliminating extra etching steps. However, if the passivation thickness is about 3 μm for example, then the spacing of the sensor capacitor fingers 45 must be increased to about 5 μm or more in order that the fringe capacitance component still represents a measurable ratio of the total capacitance. For the 4000 μm sensor structure, total capacitance is now reduced to about 27 fF, with the variable fringing component now being in the region of 3 to 5 fF. Humidity variations of 1% or 2% now produce capacitance variations of less than a femtoFarad—still detectable by the highly over-sampled differential sigma-delta high-resolution converter. 18 bits of resolution also provides a very large dynamic range, enabling the converter to easily cope with the highly variable and non-linear capacitance-versus-humidity characteristics of different oxides and different pore sizes from wafer to wafer and lot to lot.

Figure 6:
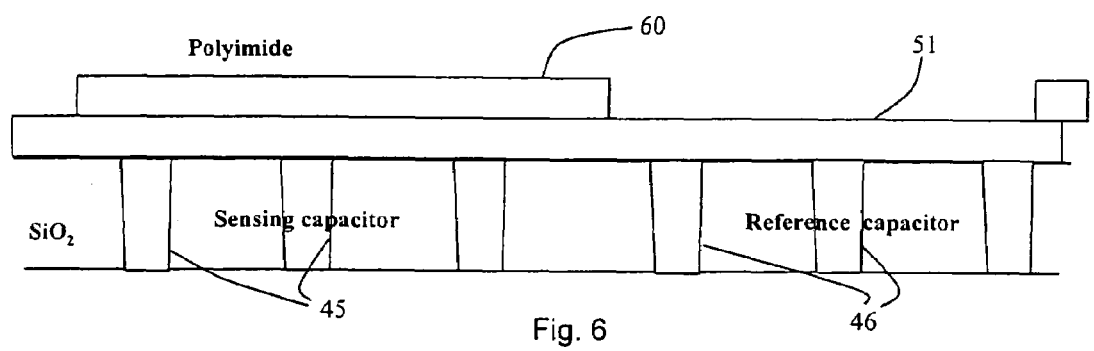
FIGS. 6 and 7 are cross-sectional views of alternative sensor components.

Referring to FIG. 6, in this embodiment, standard CMOS processing is used, with no extra processing steps required. Polyimide is often used as a 'stress relief' coating layer on silicon chips. The polyimide placement is usually determined by a slightly oversized version of the bond-pad mask. In this example, the polyimide mask includes an extra opening to eliminate polyamide 60 from over the reference capacitor. Since polyimide is porous, the portion over the sensing capacitor now experiences a minute change in capacitance versus humidity.

Figure 7:
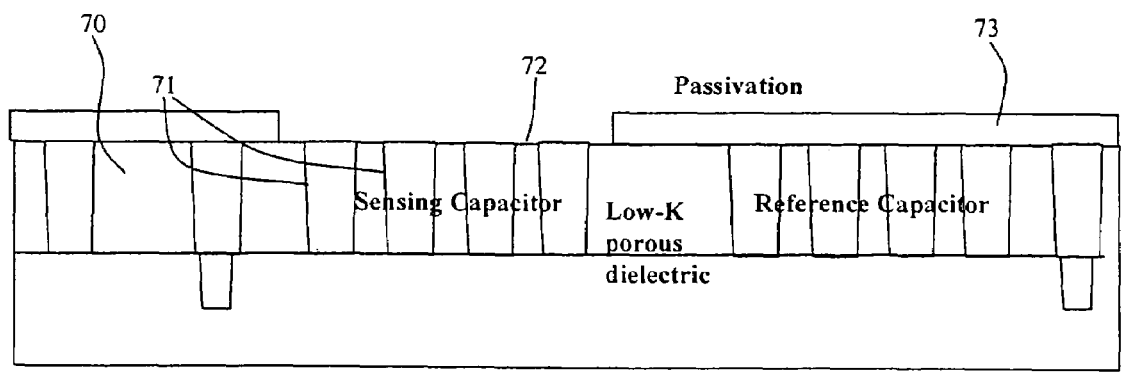

Referring to FIG. 7, in this embodiment porous low-K oxide dielectric is used in all interconnect levels of the device, so the sensor device has a porous low-K dielectric 70 between capacitive interdigitated fingers 71. By placing a 'dummy' bond pad passivation opening over the sensor structure, the surface 72 above the sensing fingers 71 is exposed for ingress of moisture into the dielectric between the fingers during the bond-pad etch. This leaves passivation 73 over the full area except the sensing capacitive fingers 71. This embodiment has the advantage of using the standard CMOS process with no extra masks required. However, it allows access by the moisture to the capacitive fingers 71. However, for many applications this is not a problem, for example a low-humidity office environment where the sensor only experiences a few millivolts applied for a few milliseconds once every few minutes.

Figure 8:
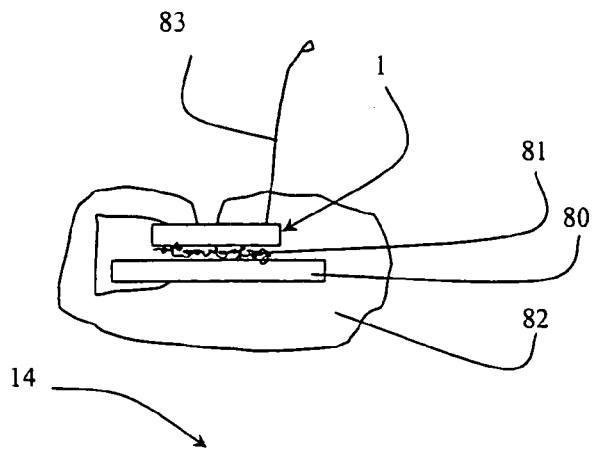
FIG. 8 is a diagram of a potting arrangement for final packaging.

FIG. 8 shows a simple potting arrangement for enclosing the single-chip wireless sensor. The sensor 1 is bonded to a battery 80 by conductive adhesive 81 and there is encapsulation 82. A former is used to keep the area over the sensing component clear. All other areas are enclosed by the encapsulant 82, which affords physical protection, as well as protection of the chip and battery terminals from corrosion or electrolytic degradation if exposed continuously to high moisture environments. No metal is exposed anywhere, except for an RF antenna wire 83.

Alternatively, there may be no encapsulation if physical protection is less important and/or if response time to temperature variations is more important.

Temperature Sensors

Figures 3A, 3B:
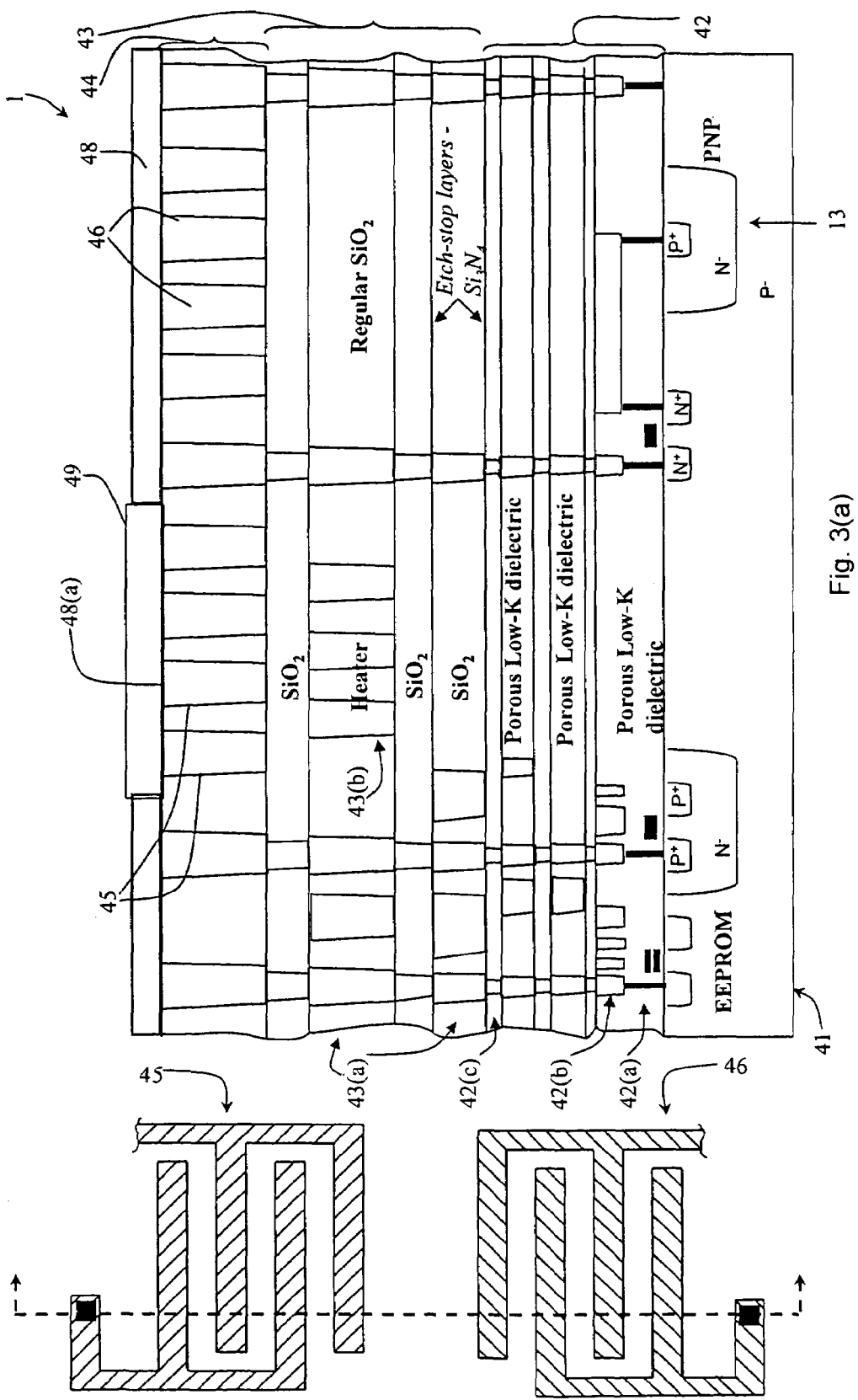
FIG. 3(a) is a cross-sectional view of the device.
FIG. 3(b) is a plan view of sensing electrodes.
Figure 3C:
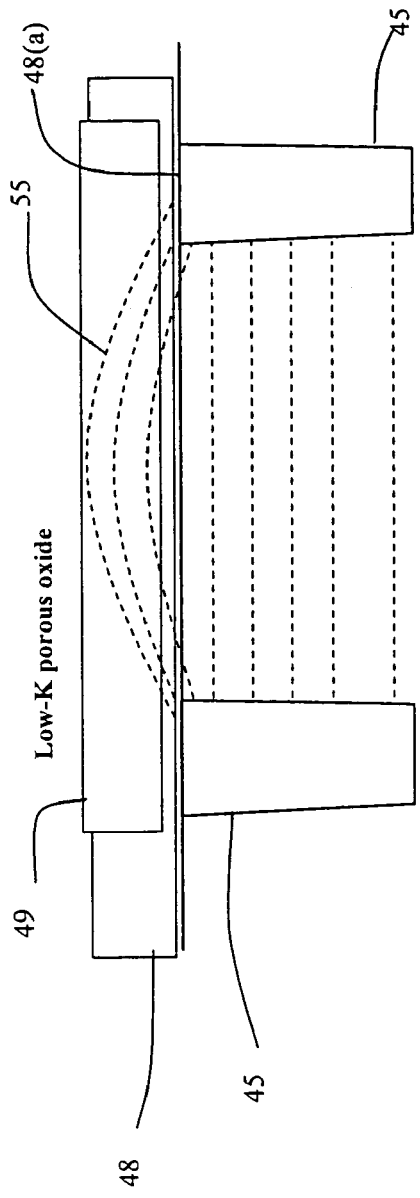
FIG. 3(c) is a diagram showing extent of a fringe field between the electrodes.

In addition to the metal heater temperature sensor 43(b) described above, a substrate PNP temperature sensor 13 is also developed as an integral part of the substrate 41, as shown in FIG. 3(a). This relies on the well-known −2.2 mV/° C. Vbe characteristic of the base emitter junction. By having a combination of humidity and temperature sensors in the one device, there can be calculation of an enhanced reading by the microcontroller, namely dew point. These, together with the microcontroller 2 and the flash memory 9 allow use of look-up tables for scaling and calibration, to achieve accuracy to within 0.5° C.

Figure 9:
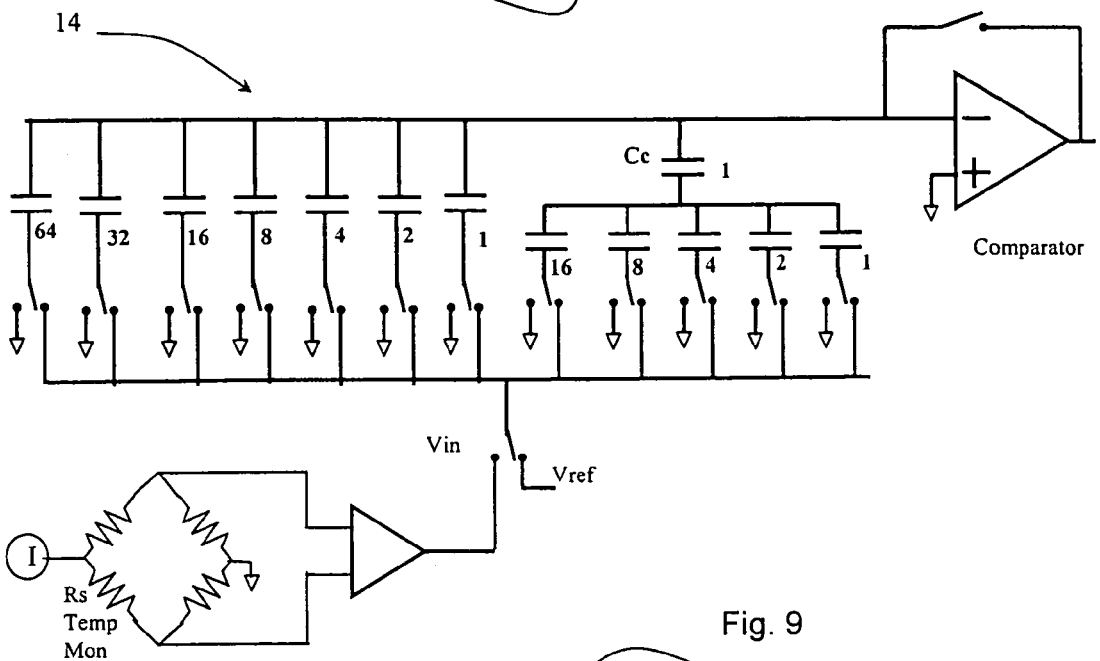
FIG. 9 is a circuit diagram of a 12-bit SAR A-to-D converter of the sensor device.
Figure 10:
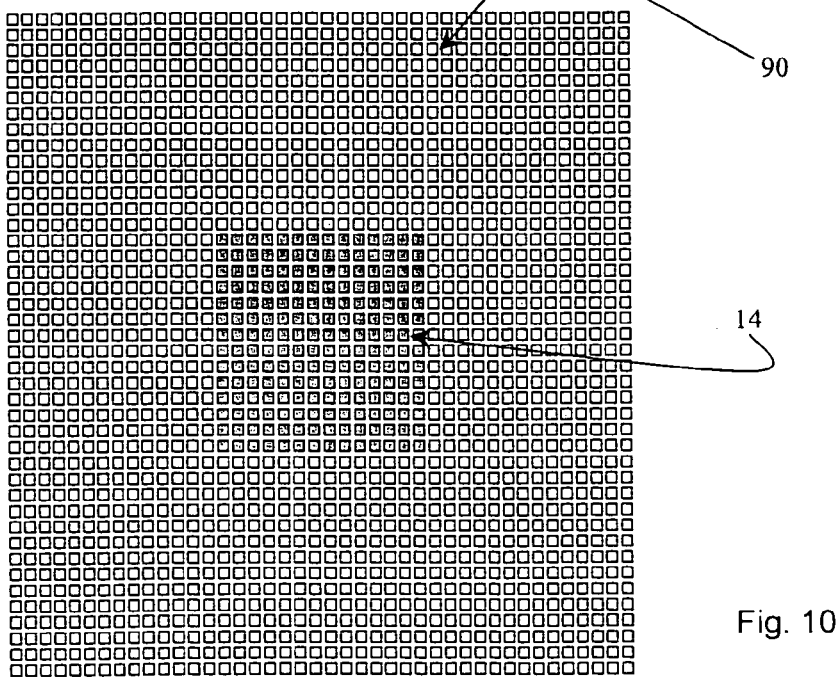
FIG. 10 is a layout view of the capacitor array for the SAR converter.

Referring to FIG. 9, the 12-bit SAR converter 14 is shown. This measures the Vbe voltage of the PNP, or the temperature-dependent resistance of the metal heater monitor in a bridge configuration as shown. The converter achieves 12 bit resolution without any calibration circuits, as follows. Referring to FIG. 10 the capacitor array for the converter 14 is in the center of the level, and it is surrounded by eight similar dummy arrays 90 to ensure constant topography and excellent matching of the key array capacitors in the converter 14. The array is segmented into 7 upper bits and a 5-bit sub-DAC via coupling capacitor Cc. This, together with a small unit capacitor size of 7×7 μm, keeps the entire array capacitance (Cs) at around 8 pF, small enough that it can be driven efficiently with an on-chip buffer amplifier as shown, and also small enough that global mismatches due to gradients in oxide thickness or other process parameters are minimized. At a sampling frequency of 100 KHz, the kT/C noise figure is 140 nV, well below the 12-bit LSB size Being on Metal 5 (fifth level), the capacitors have very small parasitic capacitances to the substrate, simplifying matching of the ratioed capacitors. The Metal-Insulator-Metal (MIM) structure of these capacitors results in low voltage and temperature coefficients and parasitic resistances.

Flash Microcontroller:

Having the 8-bit microcontroller 2 and the 64 KB Flash memory 9 on the same chip as the sensors enables significant improvements in accuracy and functionality. This is because real-time continuous calibration or in-situ calibration over various conditions of temperature is achieved. This amount of memory is also sufficient to accommodate the entire IEEE802.15.4 protocol and Zigbee software stack to perform beacon, peer-to-peer, star and mesh networking, key requirements of modern wireless sensor networks. An on-chip regulator generates 1.2V, which powers most of the microcontroller, memory blocks, and wireless RF transceiver, which are fabricated on thin-oxide minimum geometry devices.

Figure 11:
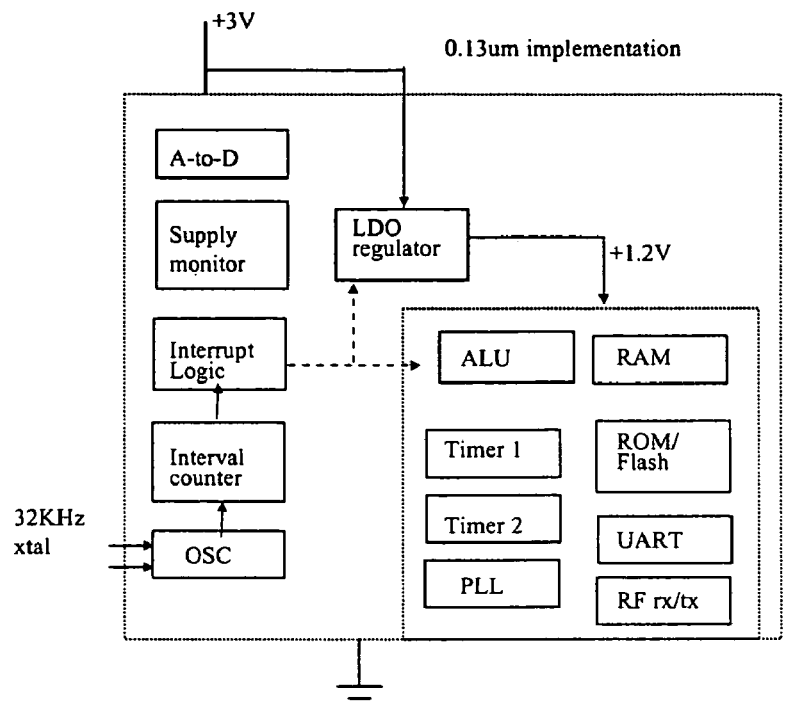
FIG. 11 is a block diagram of a microcontroller of the device.

To facilitate lower power, the time-interval counter and part of the microcontroller's interrupt logic are implemented on thick-oxide 3.3V transistors, as shown in FIG. 11. This means the regulator can be switched off when the chip is in sleep or power-down mode, eliminating the DC bias currents of the regulator. This, together with almost-zero sub-threshold leakage of the 3V transistors, results in significant power saving and elongation of battery life. On wakeup from power-down, the microcontroller also achieves reduction of noise and substrate crosstalk by operating the sensors, converters, and radio transceiver sequentially.

Figure 12:
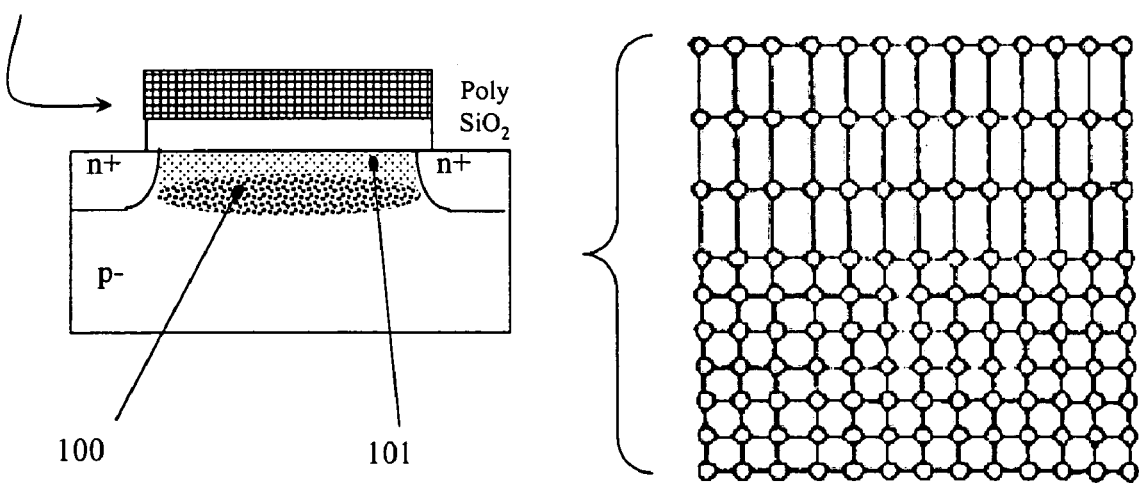
FIG. 12 is cross-sectional diagram showing a sub-surface current flow path in a strained-silicon transistor of the device.

Turning now to the wireless transceiver 3, and its low noise amplifier (LNA) in particular, the LNA is designed to have extra low power and low noise operation. This is enabled by copper inductors on the fifth or sixth levels, and the use of strained silicon MOS devices for the front-end LNA, see FIG. 12. This diagram shows a thin layer of Silicon-Germanium 100, over which there is a thin strained silicon layer 101, with higher carrier mobility than regular silicon. The polysilicon gate 102 creates a channel in the strained silicon region. However the majority of the transistor current flows in the sub-surface SiGe region, due to the higher mobility of Germanium, giving lower noise operation and higher gain. The LNA can therefore be biased at lower currents for the same gain, saving battery power. Copper has lower resistance than aluminium, giving a higher Q-factor (resulting in higher receiver gain). The fifth or sixth level of copper is also thicker (lower resistance), and further away from the substrate (less parasitic capacitances).

Figure 13:
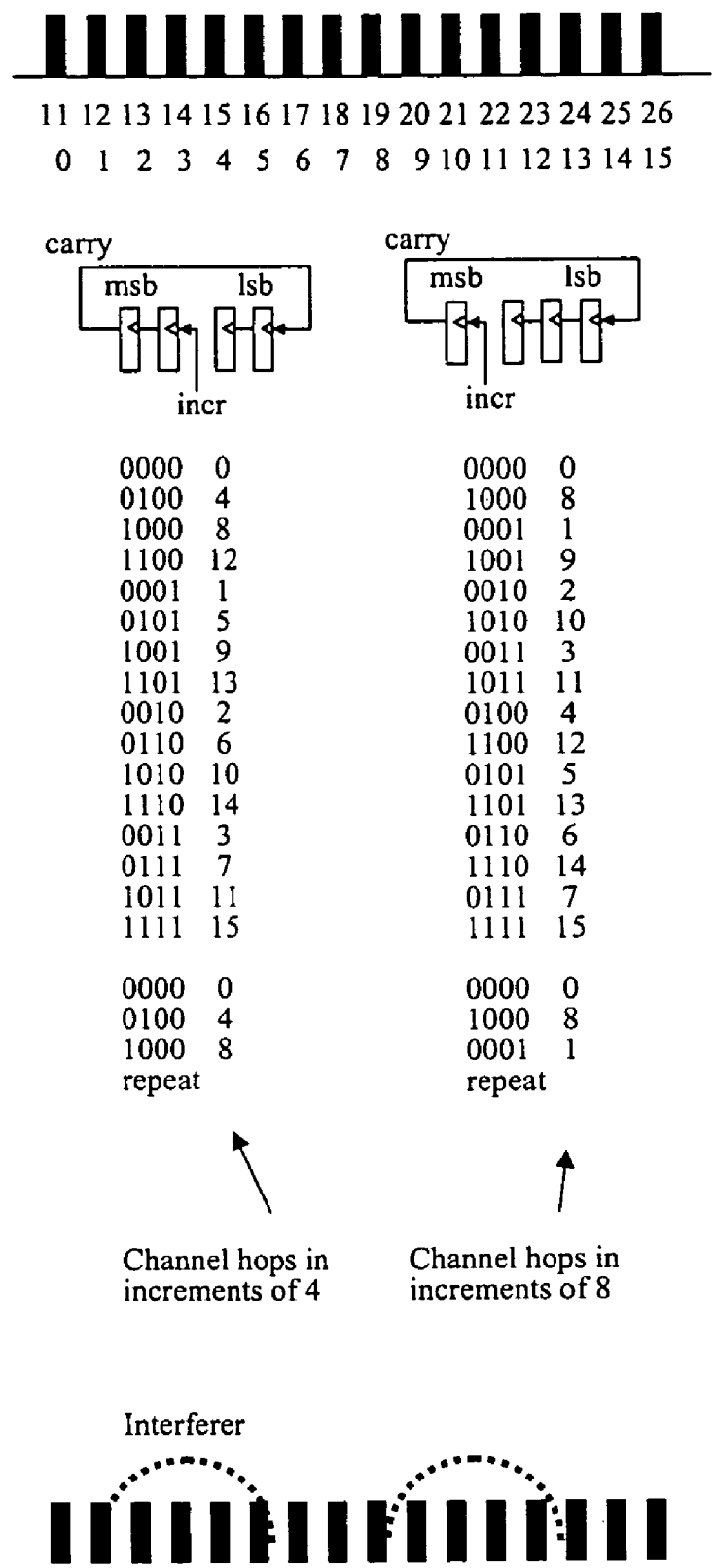
FIG. 13 is a diagram illustrating frequency selection of a wireless transceiver.

Referring to FIG. 13, frequency selection for the RF transceiver 3 is shown. The device 1 forms a node in a wireless network of nodes. This could be a simple point-to-point link or a star or mesh network. A fixed frequency is used by all nodes and the wireless interface 3 provides a slow frequency hopping scheme to circumvent interferers. It operates by all nodes using the same frequency initially. Upon a transmission failure indicating possible interference, the nodes move to a different frequency according to an algorithm illustrated in FIG. 13. There follows synchronisation of all nodes.

All nodes are pre-programmed with the hop sequence for the frequency-hopping scheme to work. Further, they must all be initialised to the same channel so that they can "hop together", typically after installation or battery replacement.

In more detail, upon installation (or battery replacement), the installer manually puts the node into "initialise" mode, by, for example, pressing a button. The node then switches on its receiver and "listens" for a nearby node transmission (or master beacon), on channel 0 for example. If it receives nothing after an appropriate time, for example a few seconds or minutes (because the current channel might be blocked), it steps to the next channel in the sequence, and again waits and listens. Eventually by this means it should receive a beacon or data packet from a neighbouring node; it can then re-synchronise its timer, request the hop interval timing, join the sequence, and go to sleep until the next hop and transmit period.

This initialisation method means the node has to stay "on" in full-power receive mode just once at installation; it can then revert to sleep mode for 99.9% of the time (as defined in the 802.15.4 standard) for the 1 to 3 year lifetime of the battery. Since the 802.15.4 standard allows for sleep periods of up to about 4 minutes, the node could be in full-power receive mode for this duration. In practice this is unlikely, however, since the installer will know about this period. Using a spectrum analyser (or hand-held wireless 'sniffer'), he can roughly predict when the next beacon transmission is due, and press the 'initialise' button just before this.

Figure 14:
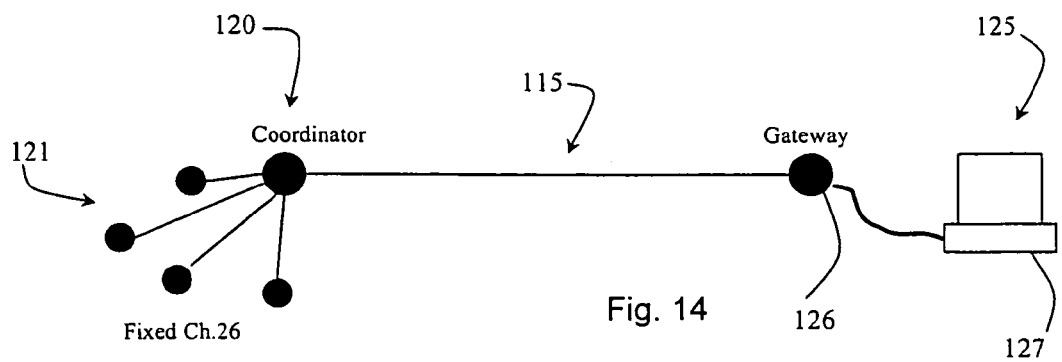
FIG. 14 shows a communication scheme for a device of the invention.

Referring to FIG. 14 this diagram shows an example of use of the slow hopping scheme. It is used on a long-distance (200 m) link 115 between two buildings 120 and 125 (using a directional 14 dBi antenna on a gateway node 126 linked with a computer 127). A standard 802.15.4 Zigbee fixed-channel star network of nodes 121 is implemented within the first building 120. This enables multi-vendor interoperable nodes to be installed in a star-network plant monitoring application, whereas the slow-hopping algorithm is employed on the long-distance critical link, which is more at risk of interference.

Testing and Calibration

This is traditionally difficult for humidity sensors, requiring special chambers of controlled humidity, along with special package handling and electrical connections.

In this invention, since the entire humidity sensor is fabricated in a standard CMOS process, it can be tested—and calibrated—at the normal wafer-level test before wafers are shipped. This takes advantage of the fact that wafer probe and factory test areas are generally operated at a precise humidity level, for example 40% relative humidity. This known value can be stored in on-chip Flash EEPROM memory for later use by the microcontroller in correctly calibrating the output value under software control, or it can be used in a non-Flash-EEPROM version of the chip to blow poly fuses to calibrate the sensor at 40% RH. This 1-point calibration may be sufficient for many applications, e.g. office air-conditioning control around a setpoint, typically 40%. If more accuracy over a wider range of humidity is desired, then a second calibration point may be required. This is achieved by doing a "second-pass" wafer probe, in an enclosed chamber at 85% RH for example, or a dry-nitrogen dessicant chamber (0.001% RH). Although the second pass wafer test adds some additional cost, it is significantly less than package based testing.

Gas Sensing

Figure 15:
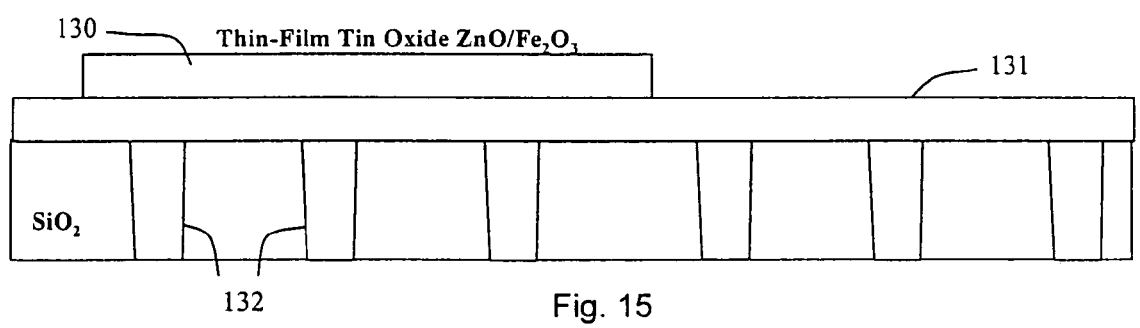
FIG. 15 is a cross-sectional diagram of a gas sensing device.

In another embodiment, illustrated in FIG. 15, a thin film 130 of zinc oxide and ferric oxide is deposited over passivation 131 at the location of one of the differential capacitors 132 of the 18-bit Sigma-Delta A-to-D converter 12. These oxides are synthesized by a sol-gel process, heated to about 120° C. to 200° C. then deposited by hybrid-ink-jet deposition. The thin-film means that small finger spacings can be used in the sensor structure, and the high-resolution A-to-D converter means that small sensor structures can be used and still result in detectable minute changes of capacitance, even at room temperature operation.

Figure 16:
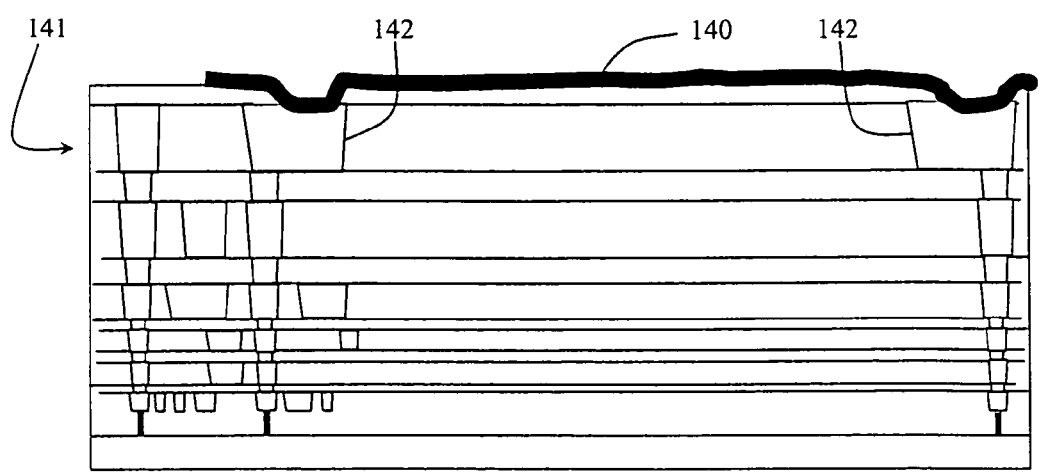
FIG. 16 is a schematic cross-sectional diagram of an audio sensor.

FIG. 16 shows an alternative embodiment, in which ferric-oxide/zinc-oxide 140 is deposited on top oxide or passivation 141, but is connected directly to electrodes 142 in the top metal layers, forming a resistor whose value can be determined as part of a bridge circuit by the 18-bit converter.

By use of different materials instead of the oxides 130 FIG. 15, the device architecture and production process may be adapted for sensing different gases, such as using palladium for hydrogen sensing, Zirconia for $SO_2$, $H_2S$, or Plasticised Polyvinyl chloride for $NO_2$, and $WO_3$ for iso-butane. In each case, both the conductivity and dielectric constant of the sensing material is changed by the ingressing gas, by adsorbtion, or physisorbtion, or chemisorbtion. Therefore the embodiments of 15—capacitive—and 16—resistive—are used alternately or together in conjunction with the on-chip tightly integrated high resolution converter to achieve very low ppm gas concentration measurements.

Audio Sensors:

Alternatively, a piezo-electric polymer may be applied in the configuration shown in FIG. 16 for sound sensitivity. Transduction is predominantly based on conductivity change. In this case, at the MOS circuit level a bridge circuit with buffer driving the 18-bit A-to-D converter is employed to capture the audio signal.

An audio sensor (microphone) is a useful feature on a remote wireless node, for example to "listen" if a motor is running, if an alarm bell is ringing. Arrangements are needed for this audio due to the 0.1% duty cycle of IEEE802.15.4; the 250 Kb/s max data rate in the 802.15.4 2.4 GHz band corresponds to a sustained constant data rate of 250 b/s at 0.1% duty cycle. A variable-bit-rate audio compressor block (VBR) is employed to achieve 15:1 or better compression ratio, achieving an effective audio bit-rate of 3.75 Kb/s—sufficient for many industrial low-grade audio requirements.

Optical Sensors

Figure 17:
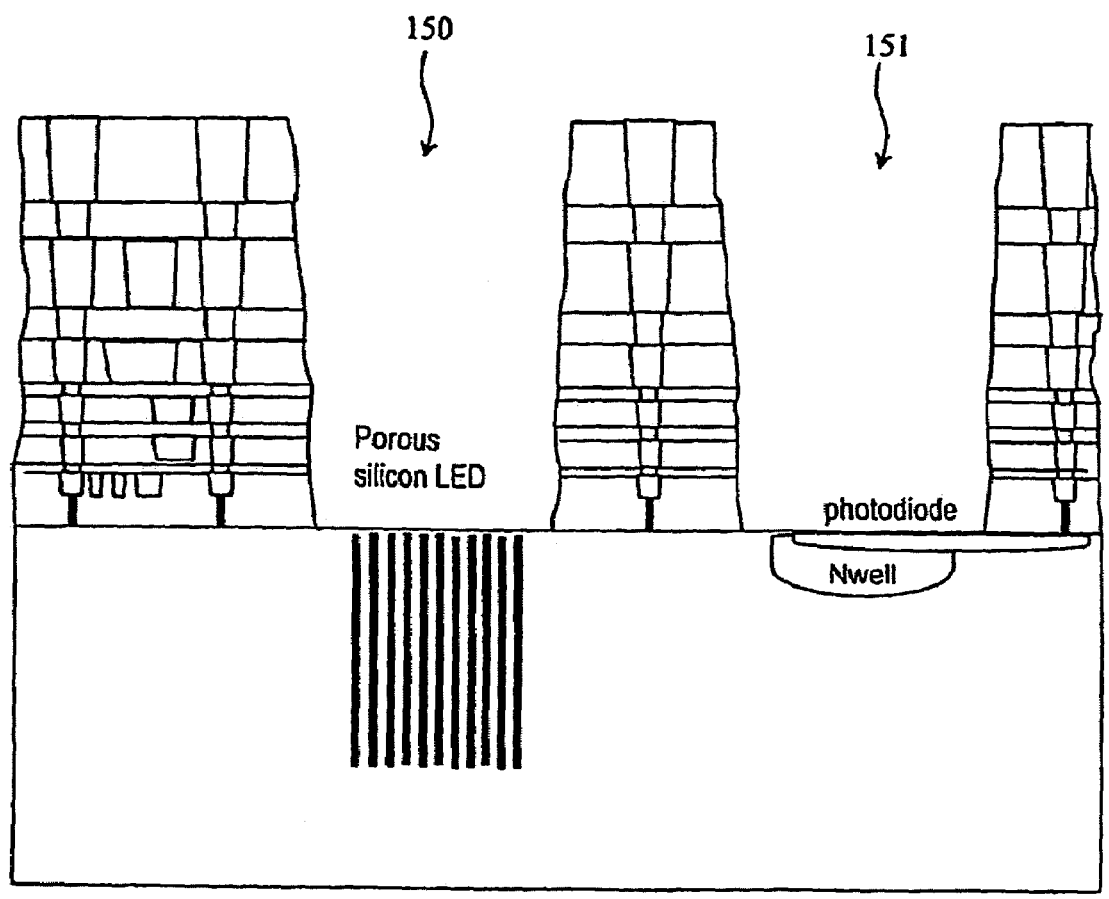
FIG. 17 is a cross-sectional view of an LED and photodiode of a device of one embodiment

Referring to FIG. 17 the device may also include an optical emitter 150 and detector 151. Highly-directional deep anisotropic etching is employed at the end of normal processing to fully etch away all six or seven layers of dielectric to expose a photodiode light sensor 151, a large PN junction, 200 um×500 um, which collects photons and generates a corresponding electrical current.

The etch also reveals a porous silicon region 150 in this embodiment, created at the start of the process by electrochemical etching of the substrate in this particular region. Passing current through this makes it function as a light emitting diode (LED) due to the well known luminescence property of porous silicon. Isolation trenches placed around the porous region can minimize any currents leaking to the substrate and improve the light efficiency.

Electrochemical etching to form porous silicon is well known to those skilled in the art, and available on some CMOS processes, but is non-standard on most CMOS processes. An alternative LED construction is a doped polymer organic light emitting device. Hybrid Ink-jet printing is used to directly deposit patterned luminescent doped-polymer films, for example polyvinylcarbazol (PVK) film, onto electrodes in the manner shown in FIG. 16.

The invention is not limited to the embodiments described but may be varied in construction and detail. For example, conductors other than copper may be used for the interconnects, such as aluminium. Also, the sensor device may be a "stripped down" version of the sensor, a "humidity-to-digital" sensor chip, having no radio or microcontroller or flash memory. In this case, calibration of the A-to-D and sensor is achieved by blowing various poly fuses in the voltage reference circuit and capacitor array. It should be noted that testing need not involve testing every code of the A-to-D, thereby simplifying testing significantly, and reducing cost. Also, some or more of the following features may be provided individually or in combination in a method and device other than as described in the embodiments above:

use of strained silicon as a low noise amplifier,
low-frequency channel selection/hopping,
SAR with replication of the capacitor array,
porous silicon LED,
audio piezo-electric polymer microphone sensor,
audio compression and transmission at low duty cycle,
the microcontroller features.

The invention claimed is:

1. An integrated sensor device comprising:
MOS circuits in a semiconductor substrate,
an interconnect stack comprising at least three interconnect levels, each interconnect level having interconnect conductors and insulating dielectric, said interconnect levels being over the substrate and interconnecting the MOS circuits,
a sensor having electrodes embedded in the interconnect dielectric and being integrally formed with the interconnect conductors, a porous material for ingress of gas or humidity being sensed,
the MOS circuits including a circuit for processing signals from the sensor electrodes, and
at least some of said circuits being located directly beneath the sensor in a vertical dimension.

2. The integrated sensor device as claimed in claim 1, wherein the sensor material includes a porous oxide interconnect dielectric at least part of which is exposed.

3. The integrated sensor device as claimed in claim 1, wherein the sensor material comprises a porous oxide interconnect dielectric, and wherein the porous oxide is carbon-doped $SiO_2$.

4. The integrated sensor device as claimed in claim 1, wherein the sensor is a capacitive sensor.

5. The integrated sensor device as claimed in claim 1, wherein the sensor porous material comprises polyimide.

6. The integrated sensor device as claimed in claim 5, wherein the sensor includes a passivation layer over the sensor electrodes.

7. The integrated sensor device as claimed in claim 5, wherein the sensor includes a passivation layer over the sensor electrodes, the polyimide is on the passivation layer, and the MOS circuits are adapted to detect changes in a fringe field between the sensor electrodes.

8. The integrated sensor device as claimed in claim 5, wherein the sensor includes a reference capacitor beneath the passivation layer.

9. The integrated sensor device as claimed in claim 5, wherein the circuits include an analogue-to-digital converter.

10. The integrated sensor device as claimed in claim 5, wherein the passivation layer is of $Si_3N_4$ composition.

11. The integrated sensor device as claimed in claim 1, wherein the sensor porous material includes a porous oxide, and wherein the sensor includes a passivation layer over the sensor electrodes.

12. The integrated sensor device as claimed in claim 11, wherein the porous oxide is on the passivation layer, and the MOS circuits detect changes in a fringe field between the sensor electrodes.

13. The integrated sensor device as claimed in claim 11, wherein the passivation layer is of $Si_3N_4$ composition.

14. The integrated sensor device as claimed in claim 11, wherein the passivation layer is recessed over the sensor electrodes.

15. The integrated sensor device as claimed in claim 11, wherein the passivation layer is recessed over the sensor electrodes, and wherein the sensor porous material is in the recess.

16. The integrated sensor device as claimed in claim 11, further comprising etch stop layers between the interconnect levels, and the passivation layer is of a same composition as the etch stop material.

* * * * *

UNITED STATES PATENT AND TRADEMARK OFFICE
CERTIFICATE OF CORRECTION

| | | |
|---|---|---|
| PATENT NO. | : 7,554,134 B2 | Page 1 of 1 |
| APPLICATION NO. | : 11/092725 | |
| DATED | : June 30, 2009 | |
| INVENTOR(S) | : Timothy Cummins | |

It is certified that error appears in the above-identified patent and that said Letters Patent is hereby corrected as shown below:

Column 10, line 54, insert --and-- after "conductors,".

Signed and Sealed this
Fifth Day of April, 2011

David J. Kappos
*Director of the United States Patent and Trademark Office*